United States Patent [19]
Hahn et al.

[11] Patent Number: 5,874,632
[45] Date of Patent: Feb. 23, 1999

[54] METHOD OF PRODUCING KETOISOPHORONE

[75] Inventors: Rainer Hahn, Karlstein; Ulrich Gora; Klaus Huthmacher, both of Gelnhausen; Frank Hübner, Ober-Ramstadt; Steffen Krill, Speyer, all of Germany

[73] Assignee: Degussa Aktiengesellschaft, Frankfurt, Germany

[21] Appl. No.: 856,859

[22] Filed: May 15, 1997

[30] Foreign Application Priority Data

May 15, 1996 [DE] Germany .................. 196 19 570.5

[51] Int. Cl.$^6$ .................................................. C07C 45/00
[52] U.S. Cl. .............................................................. 568/344
[58] Field of Search .................... 568/338, 357, 568/376, 377, 344

[56] References Cited

U.S. PATENT DOCUMENTS

| | | |
|---|---|---|
| 3,354,220 | 11/1967 | Brackman et al. . |
| 4,026,947 | 5/1977 | Costantini et al. . |
| 4,046,813 | 9/1977 | Brenner ................................... 260/586 |
| 4,092,361 | 5/1978 | Costantini ............................... 260/586 |
| 4,898,985 | 2/1990 | Ito .......................................... 568/344 |

FOREIGN PATENT DOCUMENTS

| | | |
|---|---|---|
| 669244 | 3/1966 | Belgium . |
| 2 303 785 | 10/1976 | France . |

OTHER PUBLICATIONS

Mukoyama, et al., "Preparation of Keytones by Oxidation of Olefins Using Cobalt Diketone Catalysts", Chemical Abstracts, vol. 113, No. 17, 22 Oct. 1990, Columbus, Ohio, Abstract No. 151836.

Ito, et al., "Preparation of 3,5,5–trimethyl–2–cyclohexene–1, . . . one", Chemical Abstracts, vol. 111, No. 17, 23 Oct. 1989, Columbus, Ohio, Abstract No. 153260.

*Primary Examiner*—Michael L. Shippen
*Attorney, Agent, or Firm*—Cushman Darby & Cushman IP Group of Pillsbury Madison & Sutro LLP

[57] ABSTRACT

An improved method of producing 3,5,5-trimethylcyclohex-2-ene-1,4-dione (KIP) by the oxidation of 3,5,5-trimethylcyclohex-3-ene-1-one (β-IP) in the presence of managansalene-like catalysts and certain catalytic additives.

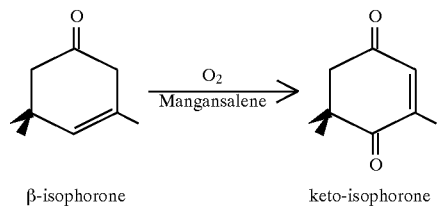

Byproducts:

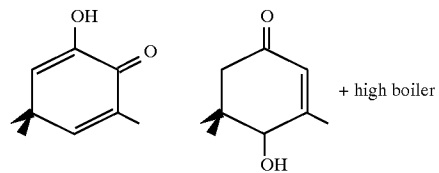

KIP is an important intermediary product in the synthesis of trimethylhydroquinone, an initial substance in the synthesis of vitamin E. Furthermore, KIP is an initial compound for the synthesis of various carotinoids.

10 Claims, 1 Drawing Sheet

METHOD OF PRODUCING KETOISOPHORONE

CROSS-REFERENCE TO RELATED APPLICATIONS

This application is based on application no. DE 19619570.5 filed in Germany on May 15, 1996, the entire disclosure of which is incorporated herein by reference.

BACKGROUND OF THE INVENTION

1. Field of the Invention

The invention relates to an improved method of producing 3,5,5-trimethylcyclohex-2-ene-1,4-dione (KIP) by the oxidation of 3,5,5-trimethylcyclohex-3-ene-1-one(β-IP) in the presence of mangansalene-like catalysts and certain catalytic additives.

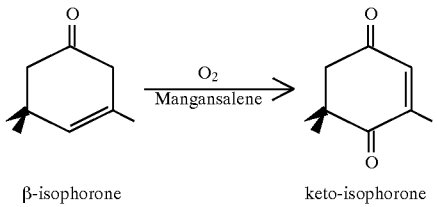

β-isophorone         keto-isophorone

Byproducts:

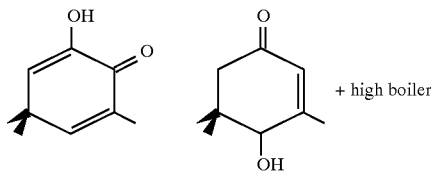

2. Background Information

KIP is an important intermediary product in the synthesis of trimethylhydroquinone, an initial substance in the synthesis of vitamin E. Furthermore, KIP is an initial compound for the synthesis of various carotinoids.

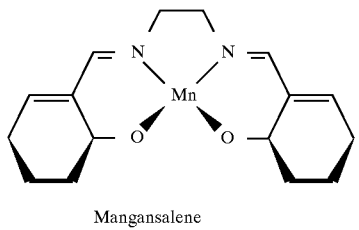

Mangansalene

State of the art

It is known that β-IP can be oxidized to KIP by molecular oxygen in the presence of a transition-metal-containing catalyst (DE-OS 24 57 157, DE-OS 38 42 547). The use of mangansalene is described in DE-OS 26 19 254.

The space-time yield (product in kg per hour and reaction volume in liters) as well as the amount of catalyst necessary for this are of decisive importance to the economy of a catalytic process. Of the above-mentioned methods for the synthesis of ketoisophorone, the reaction of β-IP with $O_2$ in the presence of mangansalene complexes of the composition shown above has the best selectivities and space-time yields.

DE-OS 26 10 254 reports in example 11 about a selectivity of homogeneous catalytic oxidation of 100%. A space-time yield (RZA) of 0.09 kg/(hr·1) can be calculated from the data contained in it. Even these not very convincing values were no longer mentioned in a scientific publication by the same authors (M. Constantini, A. Dromard, M. Jouffret, B. Brossard, J. Varagnat, *J. Mol. Catal* 1980, 7, 89–97) a few years after the public disclosure of the application. A maximal KIP selectivity of only 85% is disclosed therein, which is achieved with mangansalene as oxidation catalyst. The influence of the educt concentration on the selectivity had not been investigated previously. The problems which can occur upon an increased educt concentration (here >90%) (selectivity 55%, RZA: 0.08 kg/hr·1 (20°–23° C., $O_2$=1 bar)) can be read only from example 17 of DE-OS 26 10 254.

A disadvantage in these methods is the large amount of solvent which must be used in order to assure a high selectivity.

JP-OS 64-90150 teaches a similar method in which, however, the Mn is used in oxidation stage III in the mangansalene.

JP-OS 1-175955 possibly aims in the same direction since, according to the method it describes, the manganese complex is oxidized with tert. alkylhydroperoxides before its usage as catalyst.

SUMMARY OF THE INVENTION

It is an object of the invention to provide a method with good selectivity at a rather high concentration of β-IP. This simplifies carrying out the reaction and purifying the product KIP, thereby providing a method with increased economy.

The invention provides a method of producing 3,5,5-trimethylcyclohex-2-ene-1,4-dione (KIP) by the oxidation of 3,5,5-trimethylcyclohex-3-ene-1-one (β-IP) with molecular oxygen in the presence of mangansalene or its derivatives as catalyst, an organic base and water. The method is characterized in that a further, catalytically active compound X is added. X is selected from the group of the following compounds:

1. An organic acid with a pKa value between 2 and 7 or a corresponding aldehyde;
2. An aliphatic alcohol with $C_1$–$C_4$ atoms or phenol;
3. Compounds which can form an enol structure;
4. Lithium sulfate.

Compound X is added in a molar ratio between about 1:1 to about 100:1 to the catalyst, and the amount of β-IP is at least 15% relative to the total amount of the mixture.

At these relatively low concentrations of β-IP the reaction mixture additionally contains inert organic solvents.

β-IP is contained in the reaction mixture in an amount >15% by weight, preferably up to 40% by weight.

The reaction is generally carried out at 0° to 50° C. in the presence of the manganese-containing catalyst used in accordance with the invention (0.001 to 2% by weight relative to β-IP, preferably 0.05 to 1.0% by weight).

Water is present in an amount of 0.05 to 30% by weight relative to the total amount of the reaction mixture and the reaction is generally allowed to take place in an inert solvent in the presence of an organic, basically acting compound, especially one from the group of alkylamines, trialkylamines with $C_1$ to $C_4$ alkyl groups, including, with particular preference, triethylamine, tert. amines or 1,4-diazabicyclo[2,2,2]octane.

It is especially advantageous to add weak, organic acids and/or bidentately complexing compounds to the reaction mixture. Acetic acid, butyric acid, salicylic acid, oxalic acid, malonic acid, citric acid and other aliphatic or aromatic mono-, di- or tricarboxylic acids are especially preferable. Amino acids such as, for example, glycine, leucine, methionine or asparaginic acid are also suitable.

Aliphatic alcohols such as methanol, ethanol, butanol, isobutanol and tert-butanol or phenol also function as catalytic, selectivity-increasing additives. Compounds which can form an enol structure such as, for example, ethyl acetoacetate, phenyl acetone and especially acetyl acetone (FIG. 1) are especially advantageous. The molar ratio of catalyst:X is between 1:1 and 1:100. Even the addition of different buffer systems (buffer action between pH 6 and 9) to the water added shows a selectivity-increasing action. In addition to increasing of selectivity, a dramatic increase in the turnover number (mole product per mole catalyst) is achieved. The following inert solvents have proven to be especially advantageous: aliphatic ketones, such as acetone or methylisobutylketone, aliphatic ethers, such as ethylether diethylene glycol dimethylether and ethylene glycol dimethylether.

The production of KIP in accordance with the invention has considerable advantages over methods of the prior art:

The selectivity of the oxidation of β-isophorone at β-isophorone concentrations greater than 15% by weight is influenced by the addition of the catalytically active compound added in accordance with the invention. Yields of up to 85% are achieved at an educt concentration of 35% by weight. If β-IP is used as solvent the yield can be increased to over 72%, an increase of 17 percentage points compared to the traditional technique. This is a significant advantage in the workup of the accumulating reaction solutions.

The catalytic amounts required can be reduced even at very high concentrations of β-IP to amounts below 0.1% relative to β-IP. Without the addition of X, super-proportionally increasing catalytic amounts are necessary with increasing amounts of β-IP to achieve a complete reaction.

The space-time yield rises up to 0.5 kg/(hr·1), representing a considerable economic advantage of the reaction.

DETAILED DESCRIPTION OF THE INVENTION

EXAMPLES

Figure 1:
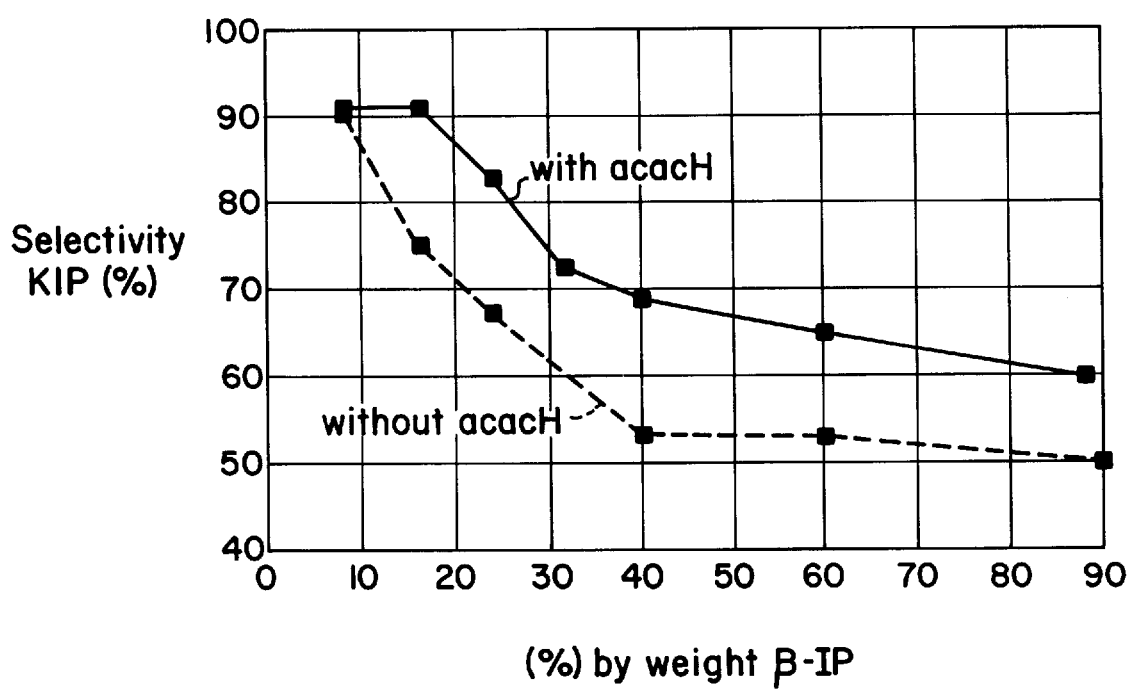
FIG. 1. Influence of acetylacetone (acacH) on selectivity. Conditions: [β-IP]/[mangansalene]=280; [acacH]/[cat]=30; [NEt$_3$]=0.30 mol/l; [water]=0.90 mol/l; solvent: Diglyme; temperature: 20° C.; oxidizing agent oxygen (1 bar).

The invention is described further in the following using exemplary embodiments.

TABLE 1

Influence of various additives on selectivity and reaction rate

| No. | Additive | Selectivity re β-isophorone | Reaction rate accd. to [after] kinetics 1$^{st}$ order in min$^{-1}$ × 10$^{-2}$ | RZA up to 80 % conversion [kg/(hr · l)] |
|---|---|---|---|---|
| 1 | without | 84% | 2.5 | 0.16 |
| 2 | acetaldehyde | 85% | 3.5 | 0.22 |
| 3 | acetylacetone | 92% | 4.4 | 0.28 |
| 4 | benzoic acid | 87% | 4.3 | 0.27 |
| 5 | acetic acid | 85% | 5.3 | 0.34 |
| 6 | ethylene glycol | 89% | 2.4 | 0.15 |
| 7 | glucose | 78% | 1.8 | 0.12 |
| 8 | lithium sulfate | 83% | 5 | 0.32 |
| 9 | nicotinic acid | 73% | 0.6 | 0.04 |
| 10 | salicylaldehyde | 85% | 4.5 | 0.29 |

Reaction conditions:

Solvent: Diglyme; base: NEt$_3$; [β-IP]=1.40 mol/l; [NEt$_3$]=0.31 mol/l; [mangansalene]=1.20 mmol/l); [H$_2$O]=0.83 mol/l; [additive]=20 mmol/l; T=35° C.; p(O$_2$)=1.0 bar

TABLE 2

Comparison of the selectivity at rising β-IP concentration with and without addition of acetylacetone

| No. | Additive | [β-IP] in (mol/l) | [cat] in (mmol/l) | [X] in (mmol/l) | selectivity re β-isophorone |
|---|---|---|---|---|---|
| 11 | acetylacetone | 0.54 | 3.79 | 113 | 91% |
| 12 | without | 0.55 | 3.87 | 0 | 90% |
| 13 | acetylacetone | 1.09 | 3.80 | 112 | 91% |
| 14 | without | 1.10 | 4.38 | 0 | 76% |
| 15 | acetylacetone | 1.63 | 5.83 | 168 | 83% |
| 16 | without | 1.65 | 5.83 | 0 | 67% |
| 17 | acetylacetone | 2.13 | 7.90 | 226 | 73% |
| 18 | without | 2.22 | 8.10 | 0 | 48% |
| 19 | acetylacetone | 2.70 | 9.59 | 279 | 69% |
| 20 | without | 2.78 | 9.84 | 0 | 53% |
| 21 | acetylacetone | 4.03 | 14.47 | 417 | 65% |
| 22 | without | 4.03 | 14.46 | 0 | 53% |
| 23 | acetylacetone | 5.86 | 20.93 | 606 | 60% |
| 24 | without | 6.28 | 20.86 | 0 | 50% |

Reaction conditions:

Solvent: Diglyme; base: NEt$_3$; [NEt$_3$]=0.31 mol/l; [mangansalene]=1.20 mmol/l; [H$_2$O]=0.88 mol/l; T=35° C. p(O$_2$)=1.0 bar; conversion of β-isophorone is 100% in all examples

TABLE 3

Examples for the solvent-free oxidation of β-isophorone in the presence of acetylacetone (AcacH)

| No. | [β-IP] in (mol/l) | [cat] in (mmol/l) | [base] in (mol/l) | [AcacH] in (mmol/l) | [H$_2$O] in (mmol/l) | selectivity re β-isophorone |
|---|---|---|---|---|---|---|
| 25 | 6.20 | 11.49 | 0.29 | 97 | 1.08 | 74% |
| 26 | 6.37 | 5.84 | 0.29 | 20 | 0.00 | 72% |
| 27 | 6.25 | 5.73 | 0.28 | 19 | 1.07 | 70% |
| 28 | 6.07 | 11.25 | 0.47 | 38 | 1.06 | 69% |
| 29 | 6.36 | 11.78 | 0.29 | 40 | 0.00 | 66% |

Reaction conditions:

Base: NEt$_3$; T=20° C.; p(O$_2$)=1.0 bar; conversion β-isophorone in all examples 100%

TABLE 4

Examples for increasing the selectivity with low β-IP concentration in various solvents (base: NEt₃)

| No. | Solvent | [β-IP] in (mol/l) | c[cat] in (mmol/l) | [base] in (mol/l) | [X] in (mmol/l) | [H₂O] | T in (°C.) | p(O₂) in (bar) | Selectivity re β-isophorone |
|---|---|---|---|---|---|---|---|---|---|
| 30 | DEGDME | 1.85 | 3.3 | 0.26 | 0.00 | 0.75 | 20 | 1.0 | 85% |
| 31 | DEGDME | 1.84 | 3.4 | 0.26 | 93 | 0.74 | 20 | 1.0 | 87% |
| 32 | MIBK | 0.60 | 2.2 | 0.34 | 0.00 | 0.83 | 23 | 1.0 | 85% |
| 33 | MIBK | 0.60 | 2.1 | 0.33 | 58.83 | 0.93 | 23 | 1.0 | 87% |
| 34 | DME | 0.60 | 2.2 | 0.33 | 0.00 | 0.94 | 23 | 0.2 | 87% |
| 35 | DME | 0.60 | 2.1 | 0.33 | 58.83 | 0.93 | 23 | 0.2 | 91% |

TABLE 5

Influence of increasing carboxylic acid concentration on the reaction selectivity

| No. | Acetate conc. in diglyme used (mg/kg) | Formate conc. in diglyme used (mg/kg) | Acid equivalent (mmol/l) | Selectivity re β-isophorone |
|---|---|---|---|---|
| 36 | 0 | 0 | 0.0 | 91% |
| 37 | 660 | 51.5 | 4.5 | 91% |
| 38 | 730 | 200 | 6.1 | 87% |
| 39 | 1504 | 0 | 9.3 | 85% |
| 40 | 1530 | 316 | 12.0 | 84% |
| 41 | 2252 | 383 | 16.9 | 83% |
| 42 | 4640 | 562 | 33.1 | 80% |

Reaction conditions:

Solvent: Diglyme; base: NEt₃; [NEt₃]=0.30 mol/l; [β-IP]=1.35 mol/l; [mangansalene]=1.25 mmol/l; [H₂O]=0.83 mol/l; T=20° C.; p(O₂)=1.0 bar.

TABLE 6

Influence of various additives on selectivity and reaction rate

| No. | Additive | Selectivity re β-isophorone | Reaction rate accd. to kinetics 1st order in min⁻¹ × 10⁻² | RZA up to 80% conversion [kg/(hr · l)] |
|---|---|---|---|---|
| 1 | without | 84% | 2.5 | 0.16 |
| 2 | acetaldehyde | 85% | 3.5 | 0.22 |
| 3 | acetylacetone | 92% | 4.4 | 0.28 |
| 4 | benzoic acid | 87% | 4.3 | 0.27 |
| 5 | acetic acid | 85% | 5.3 | 0.34 |
| 6 | ethylene glycol | 89% | 2.4 | 0.15 |
| 7 | glucose | 78% | 1.8 | 0.12 |
| 8 | lithium sulfate | 83% | 5 | 0.32 |
| 9 | nicotinic acid | 73% | 0.6 | 0.04 |
| 10 | salicylaldehyde | 85% | 4.5 | 0.29 |

Reaction conditions:
Solvent: Diglyme; base: NEt₃; [β-IP]=1.40 mol/l; [NEt₃]=0.31 mol/l; [mangansalene]=1.20 mmol/l); [H₂O]=0.83 mol/l; [additive]=20 mmol/l; T=35° C.; p (O₂)=1.0 bar

TABLE 7

Comparison of the selectivity at rising β-IP concentration with and without addition of acetylacetone

| No. | Additive | [β-IP] in (mol/l) | [cat] in (mmol/l) | [X] in (mmol/l) | selectivity re β-isophorone |
|---|---|---|---|---|---|
| 11 | acetylacetone | 0.54 | 3.79 | 113 | 91% |
| 12 | without | 0.55 | 3.87 | 0 | 90% |
| 13 | acetylacetone | 1.09 | 3.80 | 112 | 91% |
| 14 | without | 1.10 | 4.38 | 0 | 76% |
| 15 | acetylacetone | 1.63 | 5.83 | 168 | 83% |
| 16 | without | 1.65 | 5.83 | 0 | 67% |
| 17 | acetylacetone | 2.13 | 7.90 | 226 | 73% |
| 18 | without | 2.22 | 8.10 | 0 | 48% |
| 19 | acetylacetone | 2.70 | 9.59 | 279 | 69% |
| 20 | without | 2.78 | 9.84 | 0 | 53% |
| 21 | acetylacetone | 4.03 | 14.47 | 417 | 65% |
| 22 | without | 4.03 | 14.46 | 0 | 53% |
| 23 | acetylacetone | 5.86 | 20.93 | 606 | 60% |
| 24 | without | 6.28 | 20.86 | 0 | 50% |

Reaction conditions:

Solvent: Diglyme; base: NEt₃; [NEt₃]=0.31 mol/l; [mangansalene]=1.20 mmol/l; [H₂O]=0.88 mol/l; T=35° C.; p(O₂)=1.0 bar; conversion of β-isophorone is 100% in all examples

TABLE 8

Examples for the solvent-free oxidation of β-isophorone in the presence of acetylacetone (AcacH)

| No. | [β-IP] in (mol/l) | [cat] in (mmol/l) | [base] in (mol/l) | [AcacH] in (mmol/l) | [H₂O] in (mmol/l) | selectivity re β-isophorone |
|---|---|---|---|---|---|---|
| 25 | 6.20 | 11.49 | 0.29 | 97 | 1.08 | 74% |
| 26 | 6.37 | 5.84 | 0.29 | 20 | 0.00 | 72% |
| 27 | 6.25 | 5.73 | 0.28 | 19 | 1.07 | 70% |
| 28 | 6.07 | 11.25 | 0.47 | 38 | 1.06 | 69% |
| 29 | 6.36 | 11.78 | 0.29 | 40 | 0.00 | 66% |

Reaction conditions:

Base: NEt₃; T=20° C.; p(O₂)=1.0 bar; conversion β-isophorone in all examples 100%

TABLE 9

Examples for increasing the selectivity with low β-IP concentration in various solvents (base: NEt₃)

| No. | Solvent | [β-IP] in (mol/l) | c[cat] in (mmol/l) | [base] in (mol/l) | [X] in (mmol/l) | [H₂O] | T in (°C.) | p(O₂) in (bar) | Selectivity re β-isophorone |
|---|---|---|---|---|---|---|---|---|---|
| 30 | DEGDME | 1.85 | 3.3 | 0.26 | 0.00 | 0.75 | 20 | 1.0 | 85% |
| 31 | DEGDME | 1.84 | 3.4 | 0.26 | 93 | 0.74 | 20 | 1.0 | 87% |
| 32 | MIBK | 0.60 | 2.2 | 0.34 | 0.00 | 0.83 | 23 | 1.0 | 85% |
| 33 | MIBK | 0.60 | 2.1 | 0.33 | 58.83 | 0.93 | 23 | 1.0 | 87% |
| 34 | DME | 0.60 | 2.2 | 0.33 | 0.00 | 0.94 | 23 | 0.2 | 87% |
| 35 | DME | 0.60 | 2.1 | 0.33 | 58.83 | 0.93 | 23 | 0.2 | 91% |

TABLE 10

Influence of increasing carboxylic acid concentration on the reaction selectivity

| No. | Acetate conc. in diglyme used (mg/kg) | Formate conc. in diglyme used (mg/kg) | Acid equivalent (mmol/l) | Selectivity re β-isophorone |
|---|---|---|---|---|
| 36 | 0 | 0 | 0.0 | 91% |
| 37 | 660 | 51.5 | 4.5 | 91% |
| 38 | 730 | 200 | 6.1 | 87% |
| 39 | 1504 | 0 | 9.3 | 85% |
| 40 | 1530 | 316 | 12.0 | 84% |
| 41 | 2252 | 383 | 16.9 | 83% |
| 42 | 4640 | 562 | 33.1 | 80% |

Reaction conditions:

Solvent: Diglyme; base: NEt₃; [NEt₃]=0.30 mol/l; [β-IP]=1.35 mol/l; [mangasalene]=1.25 mmol/l; [H₂O]=0.83 mol/l; T=20° C.; p(O₂)=1.0 bar.

References and patents cited herein are hereby incorporated by reference.

What is claimed is:

1. A method of producing 3,5,5-trimethylcyclohex-2-ene-1,4-dione (KIP) comprising oxidizing 3,5,5-trimethylcyclohex-3-ene-1-one (β-IP) with molecular oxygen in the presence of
   (i) a catalyst selected from the group consisting of mangansalene or a mangansalene derivative;
   (ii) an organic base;
   (iii) water; and
   (iv) a catalytically active compound X selected from the group consisting of:
      (a) an organic acid with a pKa value between 2 and 7 or a corresponding aldehyde;
      (b) a compound which can form an enol structure; and
      (c) lithium sulfate.
   wherein the compound X is added in a molar ratio between 1:1 and 100:1 to the catalyst and wherein the amount of β-IP is at least 15% relative to the total amount of the mixture.

2. The method according to claim 1, wherein X is a bidentately complexing organic acid.

3. The method according to claim 1 or 2, wherein X is an aliphatic (C₂–C₆) or aromatic (mononuclear) mono-, di- or tricarboxylic acid.

4. The method according to claim 3, wherein X is acetic acid, butyric acid, salicylic acid, oxalic acid, malonic acid or citric acid.

5. The method according to claim 1, wherein the water contained in the reaction mixture is buffered to a pH of 6 to 9.

6. The method according to claim 1, wherein acetylacetone is used as catalytically active compound.

7. A method of producing 3,5,5-trimethylcyclohex-2-ene-1,4-dione (KIP) comprising oxidizing 3,5,5-trimethylcyclohex-3-ene-1-one (β-IP) with molecular oxygen in the presence of
   (i) a catalyst selected from the group consisting of mangansalene or a mangansalene derivative;
   (ii) an organic base;
   (iii) water; and
   (iv) a catalytically active compound X selected from the group consisting of an aldehyde of acetic acid, butyric acid, salicylic acid, oxalic acid, malonic acid and citric acid;
   wherein the compound X is added in a molar ratio between 1:1 and 100:1 to the catalyst and wherein the amount of β-IP is at least 15% relative to the total amount of the mixture.

8. A method of producing 3,5,5-trimethylcyclohex-2-ene-1,4-dione (KIP) comprising oxidizing 3,5,5-trimethylcyclohex-3-ene-1-one (β-IP) with molecular oxygen in the presence of
   (i) a catalyst selected from the group consisting of mangansalene or a mangansalene derivative;
   (ii) an organic base;
   (iii) water; and
   (iv) a catalytically active compound X, X being an aliphatic (C₂–C₆) amino acid;
   wherein the compound X is added in a molar ratio between 1:1 and 100:1 to the catalyst and wherein the amount of β-IP is at least 15% relative to the total amount of the mixture.

9. A method of producing 3,5,5-trimethylcyclohex-2-ene-1,4-dione (KIP) comprising oxidizing 3,5,5-trimethylcyclohex-3-ene-1-one (β-IP) with molecular oxygen in the presence of
   (i) bis(2-hydroxybenzylidene)-ethylene diamine manganese;
   (ii) an organic base;
   (iii) water; and
   (iv) a catalytically active compound X selected from the group consisting of:
      (a) an organic acid with a pKa value between 2 and 7 or a corresponding aldehyde;
      (b) an aliphatic alcohol with C₁–C₄ atoms or phenol;
      (c) a compounds which can form an enol structure; and
      (d) lithium sulfate.
   wherein the compound X is added in a mola r ratio between 1:1 and 100:1 to the catalyst and wherein the amount of β-IP is at least 15% relative to the total amount of the mixture.

10. The method according to claim 9, wherein the salene complex is used in an amount of 0.001 to 2% by weight relative to β-IP.

* * * * *